United States Patent [19]
Spitsberg et al.

[11] Patent Number: 5,905,026
[45] Date of Patent: May 18, 1999

[54] METHOD OF DETECTING EXPRESSION OF AND ISOLATING THE PROTEIN ENCODED BY THE BRCA1 GENE

[75] Inventors: Vitaly L. Spitsberg; Ronald C. Gorewit, both of Ithaca, N.Y.

[73] Assignee: Cornell Research Foundation, Inc., Ithaca, N.Y.

[21] Appl. No.: 08/703,776

[22] Filed: Aug. 27, 1996

[51] Int. Cl.$^6$ .......................... G01N 33/574; G01N 33/68
[52] U.S. Cl. ............................ 435/7.23; 436/64; 436/86; 436/813; 530/413; 530/827; 530/832
[58] Field of Search ............................. 435/7.23; 436/64, 436/86, 813; 530/413, 827, 832

[56] References Cited

FOREIGN PATENT DOCUMENTS 9633271 10/1996 WIPO.

OTHER PUBLICATIONS

Miki,Y. et al, (1994) A Stong Candidate for the Breast and Ovarian Cancer Susceptibility Gene BRCA1, Science 266, pp. 66–71.

Futreal, A et al, (1994) BRCA1 Mutations In Primary Breast and Ovarian Carcinomas, Science 266, pp. 120–126.

Tavtigian, S.V. et al, (1996) The Complete BRCA2 gene and mutations in chromosomes 13q–linked Kindreds, Nature Genetics 12, pp. 333–337.

Chen, Y et al (1995) Aberrant Subcellular Localization of BRCA1 In Breast Cancer, Science 270, pp. 789–791.

Scully, R. et al (1996), location of BRCA1 In Human Breast and Ovarian Cells, Science 272, pp. 123–124.

Thompson M.E. et al, (1996) Decreased Expression of BRCA1 Accelerates Growth and Is Often present During Sporadic Breast Cancer Progression, Nature Genetics 9, 444–450.

Jensen, R. et al, (1996) BRCA1 is Secreted And Exhibits Properties of a Granin, Nature Genetics 12, 303–308.

Spitsberg, V.S. et al (1996) Identification of Immunoreactive BRCA1 Protein in Milk and Mammary Tissue ASBMB/ASIP/AAI Joint Meeting With ASBMB Satellite Meetings. Program addendum and Late–breaking abstracts, Ernest N. Morial Convention Center, New Orleans, LA, Jun. 1–6.

Spitsberg, V.L. et al, (1995) Phosphorylation of Bovine and Human Milk Fat Globule Membrane (MFGM) and Bovine Skim Milk Membrane (SSM) proteins Effect Metals Inhibitors and Triton X–100, The FASER j. ((3)#495.

Spitsberg, V.L. et al, (1996) Is the MFGM Associated Protein Butyriphilin (Bph) a Kinase? The FASEB j. 10 , A684, #3946.

Spitsberg, V.L. et al, (1995) Association and Coexpression of Fatty Acid Binding Protein and Glycoprotein CD36 In The Bovine Mammary Gland, Eur J. Biochem. 230, 872–878.

LeGendre, N et al, (1989) Purification of Proteins and Peptides by SDS–PAGE, In Practical Guide to Protein and Peptide Purification for Microsequencing, Ed. D.T. Matsudaria, AP, pp. 49–69.

*Primary Examiner*—David Saunders
*Attorney, Agent, or Firm*—Brown, Pinnisi & Michaels, PC

[57] ABSTRACT

The present disclosure teaches that the proteins encoded by the BRCA1 and BRCA2 genes are found in the milk fat globule membranes from humans and cows. Therefore, BRCA1 and BRCA2 proteins can be isolated from milk produced by lactating animals. The level of expression of BRCA1 or BRCA2 can be determined by sampling the levels of BCRA1 or BCRA2 proteins found in the MFGM of lactating animals. The present invention also includes a method of determining the likelihood that a woman will develop breast cancer by measuring the amount of the BRCA1 or JBRCA2 expression during lactation. The detection of expression of BRCA1 or BRCA2 can be accomplished with an antibody raised specifically against BRCA1 or BRCA2 proteins, by isolating BCRA1 or BRCA2 from the milk fat globule membranes or by detecting activity of BRCA1 or BRCA2. The level of BRCA1 or BRCA2 is compared to a reference scale of propensity for breast cancer development correlated to normally active BRCA1 or BRCA2 levels. BRCA1, BRCA2, fatty acid binding proteins and phosphorylated proteins are found in the MFGM and the MFGM can be isolated from milk and provided in a form suitable for oral consumption, i.e. a tablet or capsule of separated milk fat globule membranes, a food additive, or a fortified dairy commodity.

24 Claims, No Drawings

METHOD OF DETECTING EXPRESSION OF AND ISOLATING THE PROTEIN ENCODED BY THE BRCA1 GENE

FIELD OF THE INVENTION

The invention pertains to the detection and isolation of BRCA1. More particularly, the invention pertains to the detection and isolation of BRCA1 found in milk fat globule membranes.

BACKGROUND OF THE INVENTION

It has been recently demonstrated that two genes, namely, BRCA1 encoding a 220 kDa protein, and BRCA2 encoding an approximate 420 kDa protein, are involved in hereditary breast and ovarian cancers. The BRCA1 protein contains an N-terminus a zinc finger domain, i.e. the region which can bind to DNA. The BRCA1 protein may represent one of the transcription factors, playing an important role in the differentiation of mammary gland cells. The C-terminal end of the BRCA1 is essential to normal BRCA1 function in breast epithelial cells, because patients inheriting 1853Stop develop very early onset breast cancer. The development of hereditary breast cancers can be seen as the result of mutations or deletions of the BRCA1 gene leading to the production of altered forms (truncated) of BRCA1 protein which cannot function as suppressors of cell growth (tumor suppressors).

It has been shown that the BRCA1 protein also can be involved in sporadic breast cancers. In this case, the transport of BRCA1 protein into the nucleus of cell is believed to be altered. Therefore, an accumulation of BRCA1 protein occurs in the cytoplasm of mammary gland secretory cells. Although there is some controversy regarding this hypothesis, the result cannot be ignored. It has been reported that the expression of BRCA1 in sporadic cancers is diminished. Quite recently, it was reported that BRCA1 is a secreted protein. Clustered BRCA1 proteins were detected by immunogold electron microscopy in small membrane bound vesicles in the apical cytoplasm of mammary epithelial cells. It is suggested that BRCA1 can manifest its function through the secretion and subsequent binding to the putative receptor of the same cell.

Though there is no consensus on the mechanism of action of BRCA1 we have to accept that BRCA1 is an important protein for development and differentiation of mammary gland secretory epithelial cells. Mutations or microdeletions of the BRCA1 gene or altered expression of BRCA1 mRNA and BRCA1 protein can lead to dedifferentiation with possible formation of cancer cells.

Recently, the complete sequence of the BRCA2 gene was reported. This gene encodes the protein of 3418 amino acids i.e. this protein would be about 420 kDas. Biochemical function of BRCA2 is not yet clear though the presence of regulatory signals are indicated. A mutational profile of BRCA2 differs from BRCA1 and is characterized by microdeletions rather than point mutations. The microdeletions in BRCA2 gene would explain the truncated forms of the BRCA2 protein. The 15 mutations observed so far by the Myriad group are quite distinct. This situation can complicate the development of the genetic test for the determination of predisposition to breast cancer. BRCA2 as BRCA1 has a sequence ("granin consensus") which is typical for a number of secretory proteins. The secretion of BRCA2 protein by mammary epithelial cells still has to be determined.

The protein BRCA1 is produced in mammary cells, but isolating BRCA1 from mammary cells is expensive and time consuming, such that it is entirely impractical to isolate commercial quantities of BRCA1. Therefore, it will be extremely important to develop an inexpensive method of isolating BRCA1 if it is to be used as a treatment.

One of the remarkable features of milk is its content of lipid droplets coated with proteo-lipid material. These droplets are milk fat globule membranes (MFGM). The MFGM, is composed of four layers: the thin membrane possibly derived from intracellular lipovesicles; the protein coat; the lipid bilayer, primarily derived from the apical plasma membrane and possibly secretory vesicle membranes; and the glycocalyx. Electron microscopy of the MFGM revealed that a major component of it represents membranous sheets with associated coat material; however, some MFGM also appeared as vesicles with little or no coat material. It is very likely that the synthesis of milk proteins during lactation is simultaneously accomplished by intensive synthesis of the above mentioned membrane components needed to replenish their loss by their extrusion from mammary gland secretory cells. In this sense, milk is a unique depo of the biological membranes synthesized inside the mammary secretory epithelial cells.

SUMMARY OF THE INVENTION

The methods of the present invention arose from the discovery that the protein encoded by thee BRCA1 gene is found in the milk fat globule membranes from humans and cows. Therefore, BRCAA1 protein can be isolated from milk produced by lactating animals.

The level of expression of BRCA1 can be determined by sampling the levels of BRCA1 protein found in the MFGM of lactating animals. The present invention also includes a method of determining the likelihood that a woman will develop breast cancer by measuring the amount of BCRA1 expression during lactation. The detection of expression of BRCA1 can be accomplished with an antibody raised specifically against BRCA1 protein, by isolating BRCA1 from the milk fat globule membranes or by detecting activity of BRCA1.The level of BRCA1 is compared to a reference scale of propensity for breast cancer development correlated to normally active BRCA1 levels.

The present invention also includes a method of providing BRCA1, BRCA2 and fatty acid binding proteins for oral consumption. The MFGM can be isolated from milk and provided ini a form suitable for oral consumption, i.e. a tablet or capsule of separated milk fat globule membranes or a food additive.

A more complete appreciation of the invention and the advantages thereof will be apparent as the same becomes better understood by reference to the following details of description.

DETAILED DESCRIPTION

The BRCA1 and BRCA2 proteins, products of Breast Cancer 1 gene and Breast Cancer 2 gene respectively, play an important role in a development and differentiation of mammary gland epithelial cells. These proteins are considered repressors of cell growth Genetic alterations of BRCA1 and BRCA2 genes, and consequently, the alterations of BRCA1 and BRCA2 proteins can lead to development of breast cancer. The analysis of BRCA1 and BRCA2 genes and, or their products can be used for diagnostic purposes. The genetic material, like DNA of blood cells, can be easily obtained for-the screening of the BRCA1/BRCA2 genes whereas the appropriate material of BRCA1/BRCA2 proteins for their direct diagnostic analysis can be obtained only via biopsy.

One of the discoveries of the present invention is the presence of immunoreactive BRCA1 protein (about 220 kDa) in human milk fat globule membrane (MFGM). Thus, MFGM can be used as a source for the analysis of the BRCA1 protein. Mutations, mnicrodeletions and decreased expression of BRCA1 will lead to the accumulation of this protein in MFGM in the form of truncated polypeptides or in diminished amount. The same is true about the BRCA2 protein. A method for the analysis of the BRCA1 and BRCA2 proteins in human MFGM is described herein. This analysis includes a test for identification of women with predisposition to breast cancer.

This invention dramatically increases the ease of obtaining in vivo sources of BCRA1 and BRCA2 proteins, products of Breast Cancer 1 gene and Breast Cancer 2 gene respectively. Only 100–200 ml of milk is needed to get the sufficient amount of MFGM for analysis of BRCA1 and BRCA2 proteins. Analysis of these proteins by Western immunoblotting and/or by peptide mapping can show the abnormalities in their synthesis. i.e. expression, and/or in their primary structure as a result of deletions or mutations. This test is not invasive to the patient and is easier than a genetic test. Furthermore, by analyzing the expressed protein, one can also pick up phenotypic changes in the proteins caused by changes in control genes and other genes that may still be undiscovered yet and have an affect on the BRCA1 and BRCA2 proteins. Therefore, the present invention is an important development in the evaluation of predisposition to breast cancer.

The presence of immunoreactive BRCA1 protein (about 220 kDa) in human and bovine milk fat globule membranes (MFGM) supports the idea that this protein is secretory protein. Hlowever, it does not exclude the idea that BRCA1 can function as a suppressor. In any circumstance, the detection and subsequent analysis of BRCA1 in human milk samples, i.e. in MFGM, would provide valuable information regarding the expression of BRCA1 protein in mammary gland cells. it is possible to imagine that such an analysis could become the basis for development of a test for the identification of individuals with predisposition to breast cancer and may be to ovarian cancer. Similar ideas are applicable to the analysis of BRCA2 in human MFGM.

MFGM originates from the apical plasma membrane of mammary gland epithelial cells. The protein composition of the MFGM was studied for many years. It has recently been demonstrated that the MFGM possesses intrinsic protein phosphorylation. A number of protein kinases were detected in MFGM and the novel protein kinase butyrophilin-kinase (Bph-kinase) was proposed as a main kinase in these membranes. Among the in vitro phosphorylated proteins of the human and bovine MFGM, there is phosphorylated 220 kDa protein corresponding to the position of immunoreactive BRCA 1. Therefore, the protein kinase phosphorylating the 220 kDa protein is present in MFGM.

Since the BRCA1 and BRCA2 proteins have the granin consensus sequence these proteins may belong to the secretory proteins. It is currently believed that the BRCA1 and BRCA2 proteins are secreted into milk by the mammary epithelial secretory cells during lactation period. BRCA1 was found in microvilli of apical membrane of mammary epithelial cells. Therefore, the secreted BRCA1 is associated with M1FGM. Because of this association, the BRCA1 protein can be detected and quantitated in MFGM by Western immunoblotting with appropriate antibodies and further analyzed by peptide mapping. The BRCA2 protein also be analyzed in MFGM similar to BRCA1.

1. Detection of BRCA1/BRCA2 in human MFGM by Western Immunoblotting.

100–200 ml of individual milk is used for the preparation of MFGM, as described by Spitsberg et al. (1995, Association and coexpression of fatty acid binding protein and glycoprotein CD36 in the bovine mammary gland. *Eur J. Biochem.*, 230. 872–878, incorporated herein by reference. Briefly, the milk is centrifuged at 1500–1700×g×15 min. at 5–20° C. The "fat cake" (cream layer on the top) is collected and resuspended in 200–500 ml. of distilled $H_2O$ or 10 mM phosphate buffer, pH 7.2 using a Waring blender (about 40–50 sec.), and the mixture is centrifuged at 50,000×g for 1–2 hrs. The pellet of MFGM can be easily collected and stored at −70° C. 5–10 mg of MFGM protein can be obtained from this amount of milk.

Detection of BRCA1 and IBRCA2 in MFGM is accomplished by, Western Immunoblotting as described by Spitsberg et al. (1995), incorporated herein by reference. The anti-human BRCA1 and anti-human BRCA2 can be purchased from Santa Cruz Biotechnology, Inc. (CA, USA).

By detecting levels of BRCA1 and BRCA2 expression in the MFGM in lactating women and tracking the development of breast cancer, a diagnostic test can be established for the propensity for developing breast cancer. Specifically, these proteins are known to act as suppressors of breast cancer. Therefore, a lower than normal expression of BRCA1 would indicate a likelihood of developing breast cancer. Furthermore, the diagnostic test could be taken one step further to the isolation of the proteins from the MFGM to perform activity assays on the isolated proteins to evaluate relative activity. If abnormal expression or activity is determined the patient could be provided with additional sources of BRCA1 or BRCA2.

2. Protein microseguencing of BRCA1/BRCA2 of human MFGM.

Microsequencing analysis of detected BRCA1 and BRCA2 proteins is accomplished according to the procedure described by LeGendre and Matsudaria (1989, Purification of proteins and peptides by SDS-PAGE, in *Practical Guide to protein and peptide punfication for microsequencing*. Ed. D. T. Matsudaria, pp.49–69), incorporated herein by reference. Briefly, the MFGM proteins, separated by (7.5% gel) SDS/PAGE, are transferred to PVDF membrane and after the identification of BRCA1/BRCA2 bands with Fonceau S staining, the bands are subjected to microsequencing analysis in the gas-phase sequencer (Applied Biosystems Model 470A).

3. Peptide Mapping

Detected BRCA1/BRCA2 can be digested with trypsin or CNBr-treatment. The peptide digest can be analyzed by HPLC ("peptide mapping")(procedure described by LeGendre and Matsudaria, 1989, Purification of proteins and otides by SDS-PAGE, in *Practical Guide to protein and peptide puification for microsequencing*. Ed. D. T. Matsudaria, pp.49–69, incorporated herein by reference) Comparison of the "peptide maps" from individuals considered to have normal "peptide maps" can provide identification of the individuals with a predisposition to breast cancer.

4. Quantitation of BRCA1 in human MFGM.

The best mode for quantitation of BRCA1/BRCA2 in human MFGM is Western Immunoblotting rather than by ELISA assay since it has been found that antibodies to BRCA1 also bind to the nonspecific proteins making ELESA assay less preferable. The quantitation analysis of the proteins by Western Immunoblotting are based on the use of the standard preparation of BRCA1 obtained from the pooled samples of human milk (about 1 liter) or from bovine milk (bovine BRCA1 cross-reacts with anti-human BRCA1) and (2) densitometric analysis of the immunostained BRCA1 protein relative to standard BRCA1 by using an Image Analyzer.

Two primary antibodies against BRCA1 have been used. The first was mAb against the BRCA1 5' region of exon 11, provided by Dr. W. Lee, and the second was C19-polyclonal antibody provided by Dr. R. Jensen. Both antibodies showed similar immunoblot patterns for the 213 kDa and 160 kDa species in MFGM of cow and human tissue, a weak 220 kDa and prominent 213 kDa band were found, as well as 190 kDA and 160 kDa bands with both antibodies. HRPO-immunostaining intensity of the 220 kDa and 213 kDa species was dependent upon the stage of mammary gland involution. Staining of the 190 kDa protein was not dependent upon involutionary stage. These data show that BRCA1 proteins (~213 kDa) are present in bovine mammary tissue and are secreted into milk. Their expression also appears related to the physiological state of the mammary gland.

5. Isolation of bovine MFGM from milk

The MFGM can be isolated and used as a source of BRCA1 for analysis or for production of large quantities of the protein for treatment. Furthermore, The MFGM is an excellent nutritional supplement. As an example, to isolate the MFGM 1–3 liters of bovines milk is centrifuged at 1500–1700×g×15 min. at 5–20° C. The "fat cake" (cream layer on the top) is collected and resuspended in 200–500 ml. of distilled $H_2O$ or 10 mM phosphate buffer, pHl 7.2 using a Waring blender (about 40–50 sec.). The mixture is placed in the centrifuge at 50,000×g for 1–2-hrs. The pellet of MFGM can be easily collected and stored at −70° C.

The phosphorylation of the MFGM proteins can be increased. As an example of the method of phosphorylation, 100 mg (of protein) of MFGM proteins is mixed with ATP in concentration 10–20 mM and $MgCl_2$ (5 mM) is added. The mixture is incubated 30 minutes at room temperature, and placed in the centrifuge at 50,000×g for 30 minutes (cold −4–10° C.). The pellet of the phosphorylated MFGM proteins can be collected and stored at −70° C.

The MFGM proteins can be incorporated into all the milk market commodities (cheese, fluid milk, butter, frozen desserts, bakery, confections, etc.) or incorporated into a tablet or capsule for use as a nutritional supplement. The MFGM would be predominantly separated from the fat, so it would be a good source of protein with the additional benefits of providing the proteins in the MFGM known to act as suppressors of cancers.

6. Isolation of BRCA1 from MFGM and Mammary Gland Tissues of Lactating Animals

Milk and mammary gland tissue from lactating animals are rich sources of BRCA1. BRCA1 can be isolated and purified by conventional chromatographic methods, including but not limited to, gel-filtration, HPLC, etc. Isolated BRCA1 can be used for scientific purposes and for the treatment of breast cancer. Limited proteolytic digestion of BRCA1 protein can release the active form of small peptides, which can be easily purified by HPLC. These peptides can be used as a therapeutic agents for the treatment of breast cancer.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of detecting expression of BRCA1 in a lactating animal, comprising:

a) collecting a sample of milk from said lactating animal; and b) detecting BRAC1 protein on milk fat globule membranes in said sample of milk.

2. The method of detecting expression of BRAC1 of claim 1 wherein BRAC1 protein is detected by an antibody raised specifically against BRAC1 protein.

3. The method of detecting expression of BRAC1 of claim 1 wherein BRAC1 protein is detected by isolated BRAC1 from said specifically said mild fat globule membranes.

4. The method of detecting expression of BRAC1 of claim 1 wherein BRAC1 protein is detected by detecting activity of BRAC1.

5. The method of detecting BRAC1 of claim 1 further comprising the step of performing a peptide mapping analysis of detected BRAC1 protein.

6. A method of screening lactating animals for a propensity to develop breast cancer, comprising:

a) collecting a sample of milk from said lactating animal;

b) detecting BRAC1 protein on milk fat globule membranes in said sample of milk; and c) comparing detection of BRAC1 protein in subparagraph b) to a reference scale of propensity for breast cancer development correlated to normally active BRAC1 levels.

7. The method of screening lactating animals for a propensity to develop breast cancer of claim 6 wherein BRAC1 protein is detected by an antibody raised specifically against BRAC1 protein.

8. The method of screening lactating animals for a propensity to develop breast cancer of claim 6 wherein BRAC1 protein is detected by isolating BRAC1 from said milk fat globule membranes.

9. The method of screening lactating animals for a propensity to develop breast cancer of claim 6 wherein BRAC1 proteins is detected by detecting activity of BRAC1.

10. The method of detecting expression of BRAC1 of claim 6 further comprising the step of performing a peptide mapping analysis of detected BRAC1 protein.

11. A method of isolating BRAC1 protein comprising:

a) collecting a sample of milk from a lactating animal; and b) separating and purifying BRAC1 from milk fat globule membranes in said sample of milk.

12. The method of isolating BRAC1 protein of claim 11 further comprising isolating said milk fat globule membranes from said sample of milk prior to said purification of BRAC1.

13. The method of isolating BRAC1 protein of claim 11 further comprising increasing phosphorylation of said BRAC1 protein.

14. A method of detecting expression of BRAC2 in a lactating animal, comprising:

a) collecting a sample of milk from said lactating animal; and b) detecting BRAC2 protein on milk fat globule membranes in said sample of milk.

15. The method of detecting expression of BRAC2 of claim 14 wherein BRAC2 protein is detected by an antibody raised specifically against BRAC2 protein.

16. The method of detecting expression of BRAC2 of claim 14 wherein BRAC2 protein is detected by isolating BRAC2 from said milk fat globule membranes.

17. The method of detecting expression of BRAC2 of claim 14 further comprising the step of performing a peptide mapping analysis of detected BRAC2 protein.

18. A method of screening lactating animals for a propensity to develop breast cancer, comprising:

a) collecting a sample of milk from said lactating animals;

b) detecting BRCA2 protien on milk fat globule membranes in said sample of milk; and c) comparing detection of BRAC2 protein in subparagraph b) to a reference scale of propensity for breast cancer development correlated to normally active BRAC2 levels.

19. The method of screening lactating animals for a propensity to develop breast cancer of claim 18 wherein BRAC2 protein is detected by an antibody raised specifically against BRAC2 protein.

20. The method of screening lactating animals for a propensity to develop breast cancer of claim 18 wherein BRAC2 protein is detected by isolating BRAC2 from milk fat globule membranes.

21. The method of detecting expression of BRAC2 of claim 18 further comprising the step of performing a peptide mapping analysis of detected BRAC2 protein.

22. A method of isolating BRAC2 protein comprising:

a) collecting a sample of milk from a lactating animal; and b) separating and purifying BRAC2 from milk fat globule membranes in said sample of milk.

23. The method of isolating BRAC2 protein of claim 22 further comprising isolating said milk fat globule membranes from said sample of milk prior to said purififcation of BRAC2.

24. The method of isolating BRAC2 protein of claim 22 further comprising increasing phosphorylation of said BRAC2 protein.

* * * * *

UNITED STATES PATENT AND TRADEMARK OFFICE
CERTIFICATE OF CORRECTION

PATENT NO. : 5,905,026

DATED : May 18, 1999

INVENTOR(S) : Vitaly L. Spitsberg

It is certified that error appears in the above-identified patent and that said Letters Patent is hereby corrected as shown below:

On the title page, Item [75], delete "Ronald C. Gorewit".

Signed and Sealed this

Fifth Day of October, 1999

Attest:

Q. TODD DICKINSON

Attesting Officer

Acting Commissioner of Patents and Trademarks